US00PP22089P3

(12) United States Plant Patent

Jones et al.

(10) Patent No.: US PP22,089 P3

(45) Date of Patent: Aug. 23, 2011

(54) FLOWERING DOGWOOD TREE NAMED 'NM1'

(50) Latin Name: *Cornus Florida*
Varietal Denomination: NM1

(76) Inventors: Jeff Jones, New Market, AL (US); Sheryl Jones, New Market, AL (US)

( * ) Notice: Subject to any disclaimer, the term of this patent is extended or adjusted under 35 U.S.C. 154(b) by 0 days.

(21) Appl. No.: 12/592,831

(22) Filed: Dec. 3, 2009

(65) Prior Publication Data

US 2011/0138509 P1 Jun. 9, 2011

(51) Int. Cl.
*A01H 5/00* (2006.01)

(52) U.S. Cl. ..... Plt./220

(58) Field of Classification Search ..... Plt./220
See application file for complete search history.

(56) References Cited

U.S. PATENT DOCUMENTS

| | | | |
|---|---|---|---|
| PP3,993 | P | 12/1976 | Steppe |
| PP4,300 | P | 9/1978 | Wills |
| PP4,627 | P | 1/1981 | Boyd |
| PP6,195 | P | 6/1988 | Lowry et al. |
| PP6,305 | P | 9/1988 | Nicholson |
| PP6,320 | P | 10/1988 | Nicholson |
| PP7,204 | P | 3/1990 | Orton, Jr. |
| PP7,205 | P | 3/1990 | Orton, Jr. |
| PP7,207 | P | 3/1990 | Orton, Jr. |
| PP7,210 | P | 4/1990 | Orton, Jr. |
| PP7,732 | P | 12/1991 | Orton, Jr. |
| PP8,500 | P | 12/1993 | Smith |
| PP8,518 | P | 12/1993 | Phillips |
| PP8,676 | P | 4/1994 | Yamashita et al. |
| PP9,283 | P | 9/1995 | Schmidt |
| PP10,166 | P | 12/1997 | Nicholson |
| PP10,423 | P | 6/1998 | Stanley |
| PP13,069 | P2 | 10/2002 | Simmen |
| PP13,098 | P2 | 10/2002 | Windham et al. |
| PP13,099 | P2 | 10/2002 | Windham et al. |
| PP13,165 | P2 | 11/2002 | Windham et al. |
| PP13,384 | P3 | 12/2002 | Lipka |
| 6,677,510 | B2 | 1/2004 | Windham et al. |
| PP15,219 | P3 | 10/2004 | Orton et al. |
| PP16,309 | P3 | 3/2006 | Orton et al. |
| PP17,768 | P3 | 5/2007 | Orton et al. |

*Primary Examiner* — Susan McCormick Ewoldt

(74) *Attorney, Agent, or Firm* — Polster, Lieder, Woodruff & Lucchesi, LC

(57) ABSTRACT

A Flowering Dogwood named 'NM1' having a pink bracts that fade to white over the bloom period, vigorous upright growth with good branching, and mildew resistance and also capable of being reproduced reliably by vegetative propagation.

9 Drawing Sheets

Latin name: *Cornus Florida.*

BRIEF SUMMARY OF THE INVENTION

The present invention relates to a new and distinct variety of *Cornus Florida* Flowering Dogwood, referred by its varietal name 'NM1'.

Discovery

I discovered my Flowering Dogwood tree 'NM1' in the summer of 1999 growing in a production area of a tree nursery in New Market, Madison County, Ala., among a group of cultivated Flowering Dogwood trees. These seedlings were grown from seed planted in the fall of 1997 as understock for budding. The seedlings were thinned and budded in August, 1998. In the spring of 1999, the seedlings were cut back to the bud and the suckers were removed. By the summer of 1999, one tree was growing much faster than the other seedling understocks. This tree was marked and observed until it flowered for the first time in the spring of 2002. After observing the unique coloration of the bracts, I began budding the new tree in August, 2002.

Propagation

'NM1' was asexually propagated, by T budding, at my direction in August, 2002. This propagation and the resulting progeny have proven the characteristics of my new variety of Flowering Dogwood tree to be firmly fixed. Further, these observations have confirmed that my new variety of tree represents a new and improved variety of Flowering Dogwood as particularly evidenced by the pink bracts that fade from pink to white over the bloom period, vigorous upright growth with good branching and mildew resistance, and which can be reliably asexually propagated.

Uniqueness

My Flowering Dogwood tree 'NM1' was observed to have pink bracts that fade to white over the bloom period, vigorous upright growth with good branching, and mildew resistance. These characteristics distinguish my new tree from other typical seedling Flowering Dogwood trees and the known cultivars.

Use

'NM1' was observed for a period of time and is believed to be particularly useful as a specimen tree or in groupings in commercial and residential areas, as well as in parks or natural areas where a small, native, flowering tree is needed. Because of its vigor and mildew resistance, my tree 'NM1' will benefit commercial growers who will be able to produce, larger, healthier liners in a short time period using fewer inputs.

BRIEF SUMMARY OF THE INVENTION

Flowering Dogwoods trees are popular trees, and a substantial number of them are planted and grown each year. Although primarily known for their spring flowering, the trees also have good summer habit, excellent fall color, and produce ornamental berries in the fall which are a source of food for many bird species. The Flowering Dogwood is typically a small, lower-branched tree with spreading branches. With age, the tree develops a flat-topped crown that is wider rather than higher, and the branches create a layered effect that is attractive in the landscape. I expect my tree 'NM1' to have a habit typical of the species. My new cultivar differs from the species in that it has pink bracts that fade to white over the bloom period, vigorous upright growth with good branching, and mildew resistance.

Silvics of North America: 1. Conifers; 2. Hardwoods. Agriculture Handbook 64 cites the native range of the Flowering Dogwood tree as extending from southwestern Maine west to New York, southern Ontario, central Michigan, central Illinois, and central Missouri and south into southeastern Kansas, eastern Oklahoma, eastern Texas and north Florida. A variety of the species also grows in the mountains of Nuevo León and Veracruz, Mexico. Pink-flowering dogwood trees are often considered to be slightly less hardy to cold weather conditions than white-flowering forms of the tree, but I expect my tree 'NM1' to be adaptable over most of the above noted range for the tree.

Flowering Dogwood is an understory tree found growing in a wide range of soil conditions, but the tree does best in well-drained soils with sufficient moisture. The tree has a fibrous but shallow root system, and grows poorly in low areas with inadequate drainage, or on long ridges and slopes with inadequate moisture. These preferences are reflected in the cultural requirements that need to be met in various landscaping situations. Due to its vigor in a nursery setting, I expect my new tree to perform well in any environment there dogwood trees typically grow.

Industry Representation

Cultivated Flowering Dogwood trees are represented in the industry by many cultivators and seedling material. Millions of *Cornus Florida* are grown, and there has been ample opportunity for improvement of the species. In Dogwoods, 2005, Capiello and Shadow list 131 cultivars, 2 varieties, 1 subspecies, and 1 form of *Cornus Florida*. Of these, *Cornus Florida* var. *rubra* represents pink-flowering seedling material. From the variety, and hybrids of this variety and white flowering *Cornus Florida,* at least 41 selections have been made. Of the selections listed in Dogwoods, bract color is described variously as pale pink, light pink, clear pink, medium pink, rich pink, deep pink, deep pink-red, deep red-pink, deep red, purple-red with color patterns that can range from tinges of pink along the margins of a bract, pink or red bract tips, red or pink bracts with pink or white centers, pink bracts with white tips, and even white bracts with pink spotting. There are 24 patented varieties of Flowering Dogwood, and of these 24, 11 are described as having some form of pink flower. However, none of these known cultivators or seedlings material exhibits pink bracts which fade to white over time such as occurs on my tree 'NM1'.

Most cultivars and seedlings of *Cornus Florida* are best characterized as small, spreading trees which attain a height of 20-30 feet with an equal or greater spread. My new tree, which is 10 years old, is 11 feet tall, 8 feet wide, and has a trunk diameter of 3.75 inches. My new tree 'NM1' has been a source of budwood for propagation, and frequent pruning has slowed its growth rate. Field grown progeny of my tree, which are 5 years old, are 11 feet tall and 6 feet wide, and have a trunk diameter of 2.5 inches. I expect that my new tree 'NM1' to have a size and shape typical of most dogwood seedlings and cultivars.

BRIEF DESCRIPTION OF THE SEVERAL VIEWS OF THE DRAWINGS

The accompanying photographs depict the color of the tree and foliage of my new variety as nearly as is reasonably possible to make the same in a color illustration of this character.

DESCRIPTION OF THE PREFERRED EMBODIMENT

The following is a detailed description of my new variety of Flowering Dogwood with color terminology in accordance with The Royal Horticulture Society Colour Chart (R.H.S.) except where the context indicates a term having its ordinary dictionary meaning. My new tree has not been observed under all growing conditions and variations may occur as a result of different growing conditions. All progeny of my new variety of flowering dogwood tree, insofar as have been observed, have been identical in all the characteristics described below.

Other than as set forth below, as of this time, no other characteristics of my new 'NM1' Flowering Dogwood tree have been observed by the inventor.

Parentage: Seedling of unknown parentage grown from collected seed planted in the fall of 1997 for liner understock.

Locality where grown and observed: A nursery in New Market, Madison county, Ala.

Figure 6:
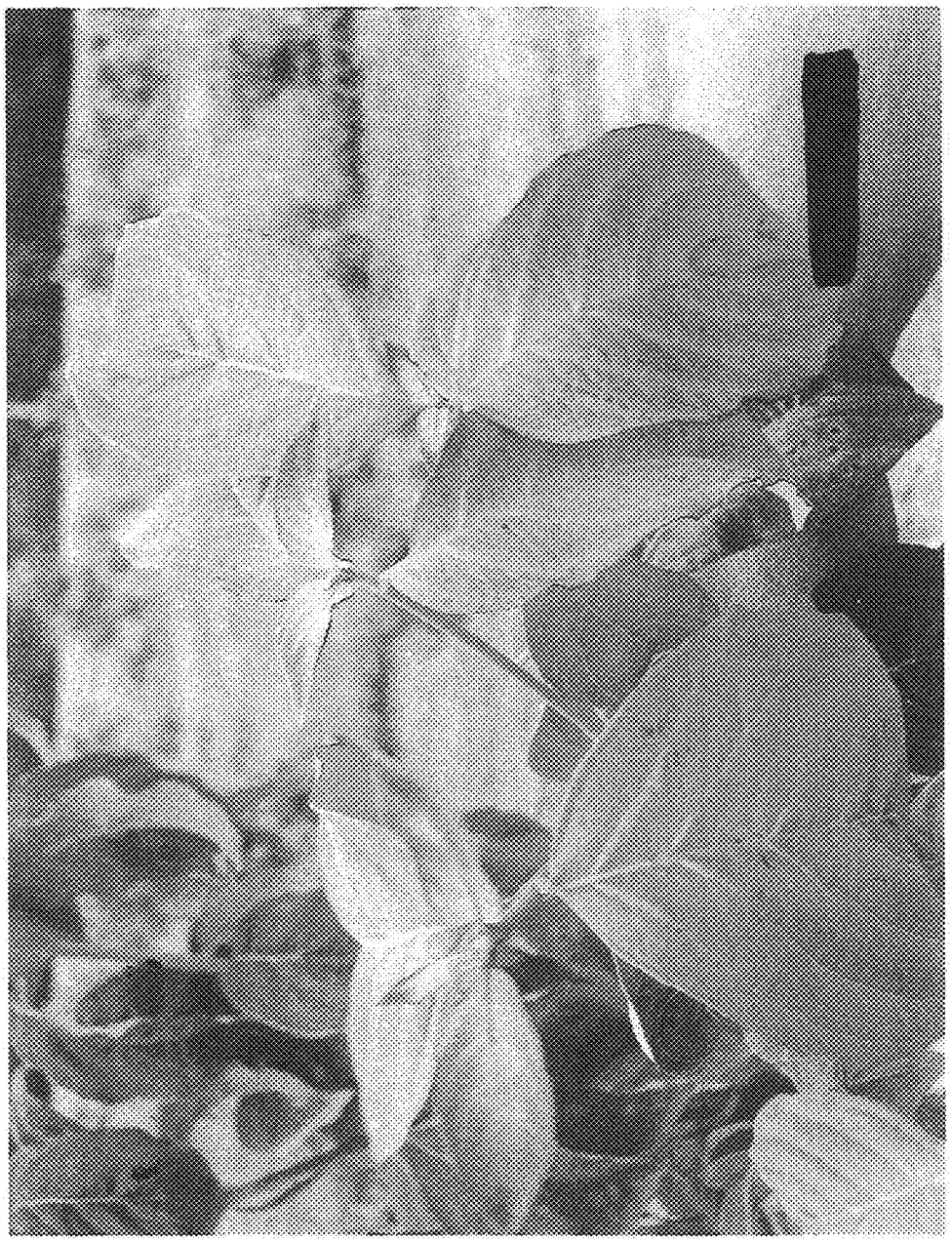
FIG. 6 depicts the new foliage growth.
Figure 7:
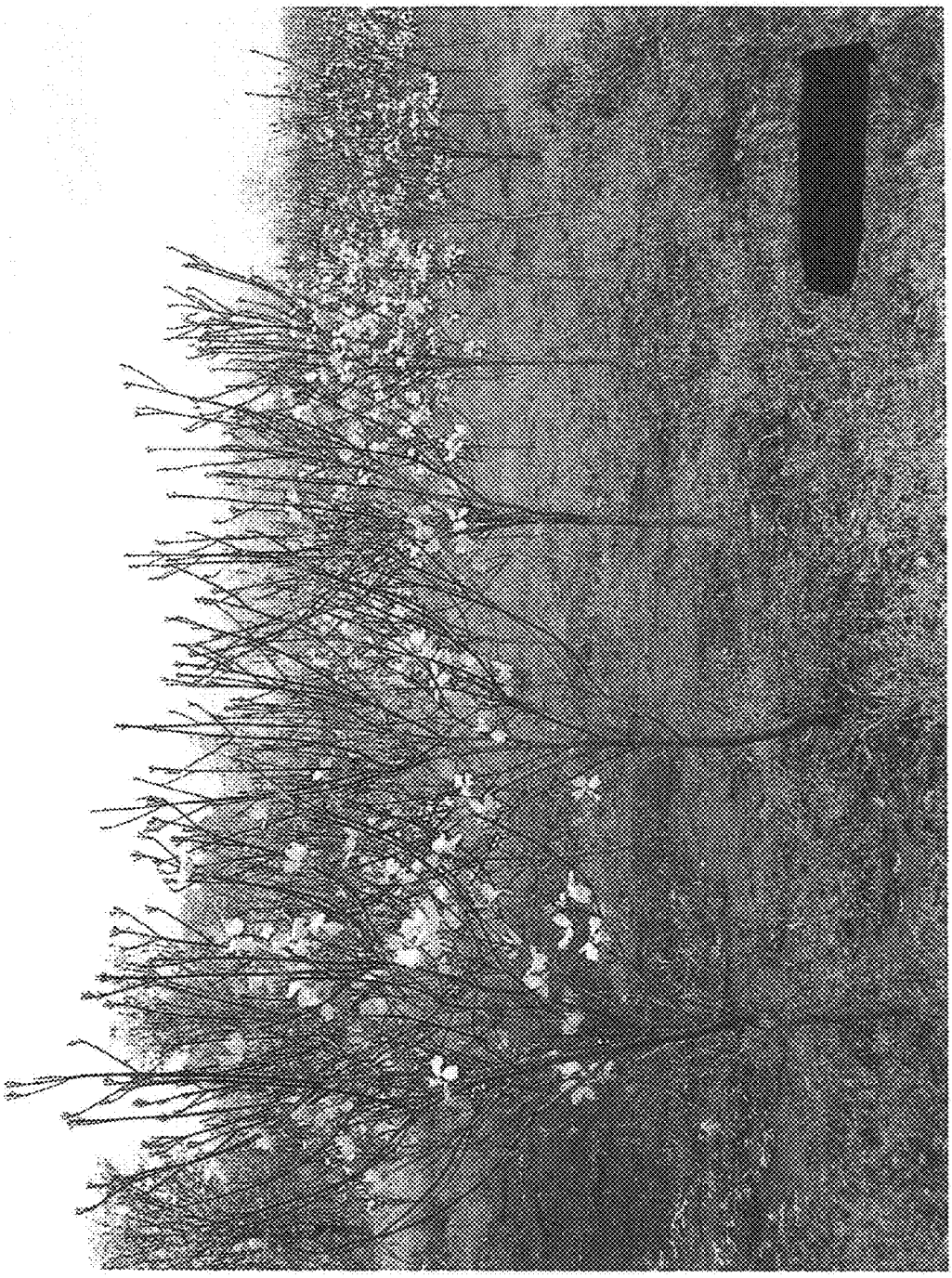
FIG. 7 depicts the early spring habit and consistency.
Figure 8:
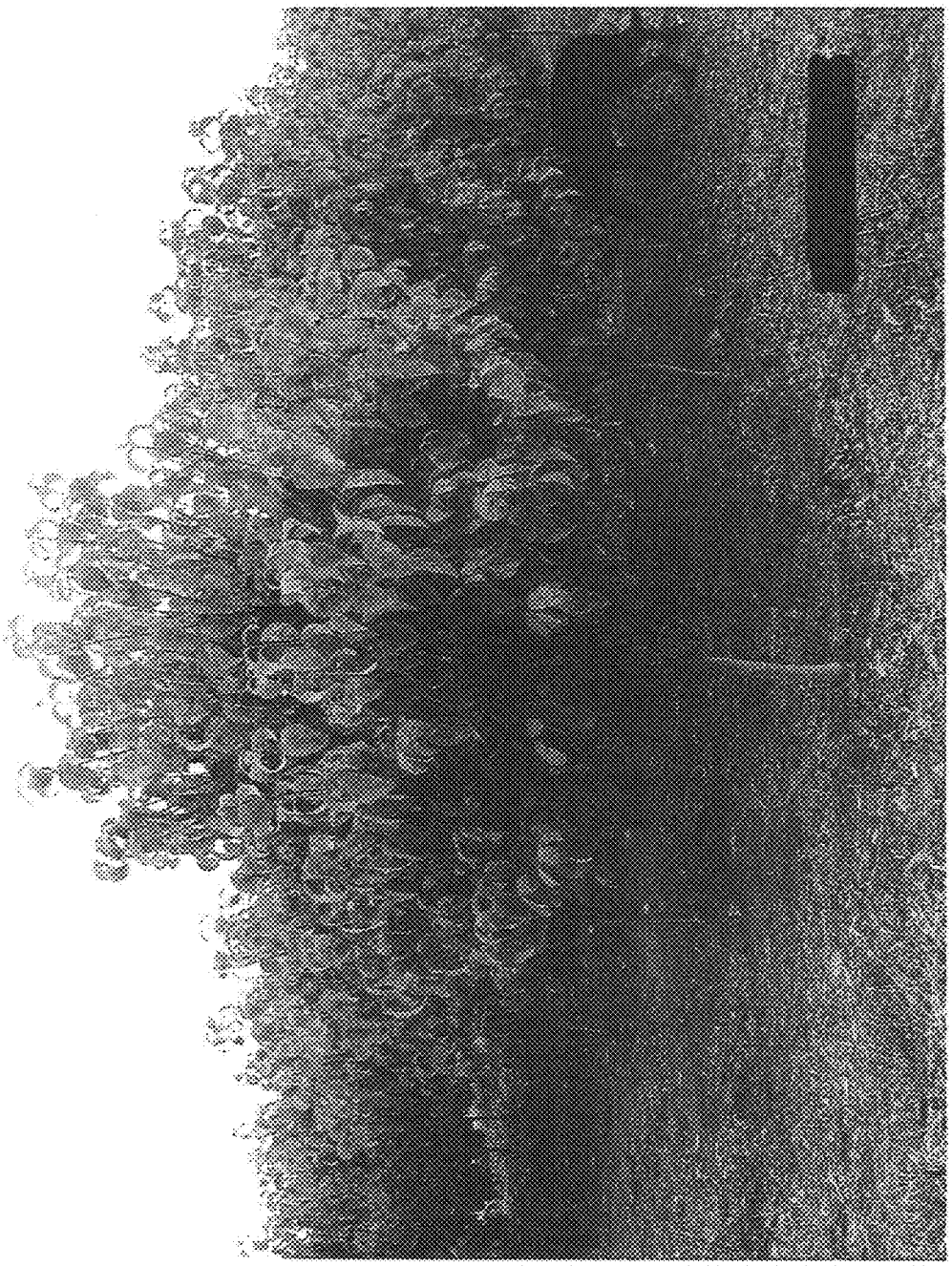
FIG. 8 depicts the summer habit and consistency.
Figure 9:
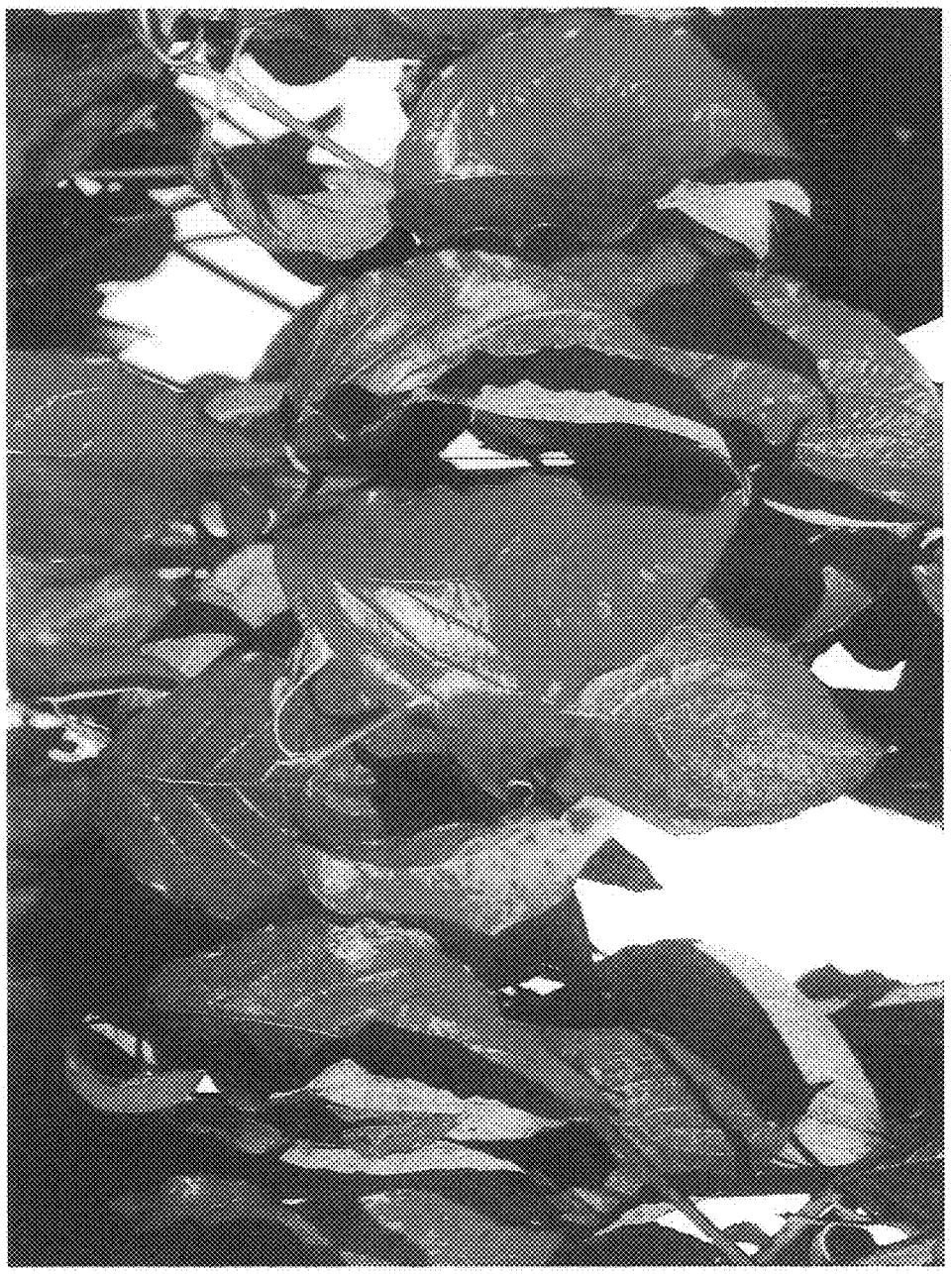
FIG. 9 depicts the fall color of the foliage.

Leaves: Typical of these species: opposite, simple, oval or ovate, broad cuneate to rounded, acuminate, smooth 1½ to 3 inches wide by 3 to 6 inches long; nearly glabrous green (RHS 143A) above, glaucous beneath some pubescence on the veins. Venation is arcuate with the major veins running parallel and longitudinally from the midrib of a leaf to its apex. Pink Flowering Dogwoods usually have reddish bronze new growth; while, white Flowering Dogwoods have a light green new growth. My new tree exhibits reddish (RHS 180B) new growth with yellowish (RHS 160B) veins which mature to green as shown in FIG. 6. This is an intermediate form between the typical pink and white forms. Fall color is typical of the species: red to reddish-purple (RHS 62D) as shown in FIG. 9.

Petiole: ¼ to ¾ inch long, yellow-green (RHS 144B).

Buds: Typical of the species: vegetative buds are small, valvate, slender, and nearly hidden by the leaf scar in winter. Bud color is grey-green (RHS 188B) becoming greener (RHS 191C) as they open. The flower buds are usually at the end of the stem, globose, flattened, valvate, and covered by two (2) pubescent outer scales and two (2) inner scales. These four scales become the bracts. The flower buds are grey (RHS 188A).

Figure 1:
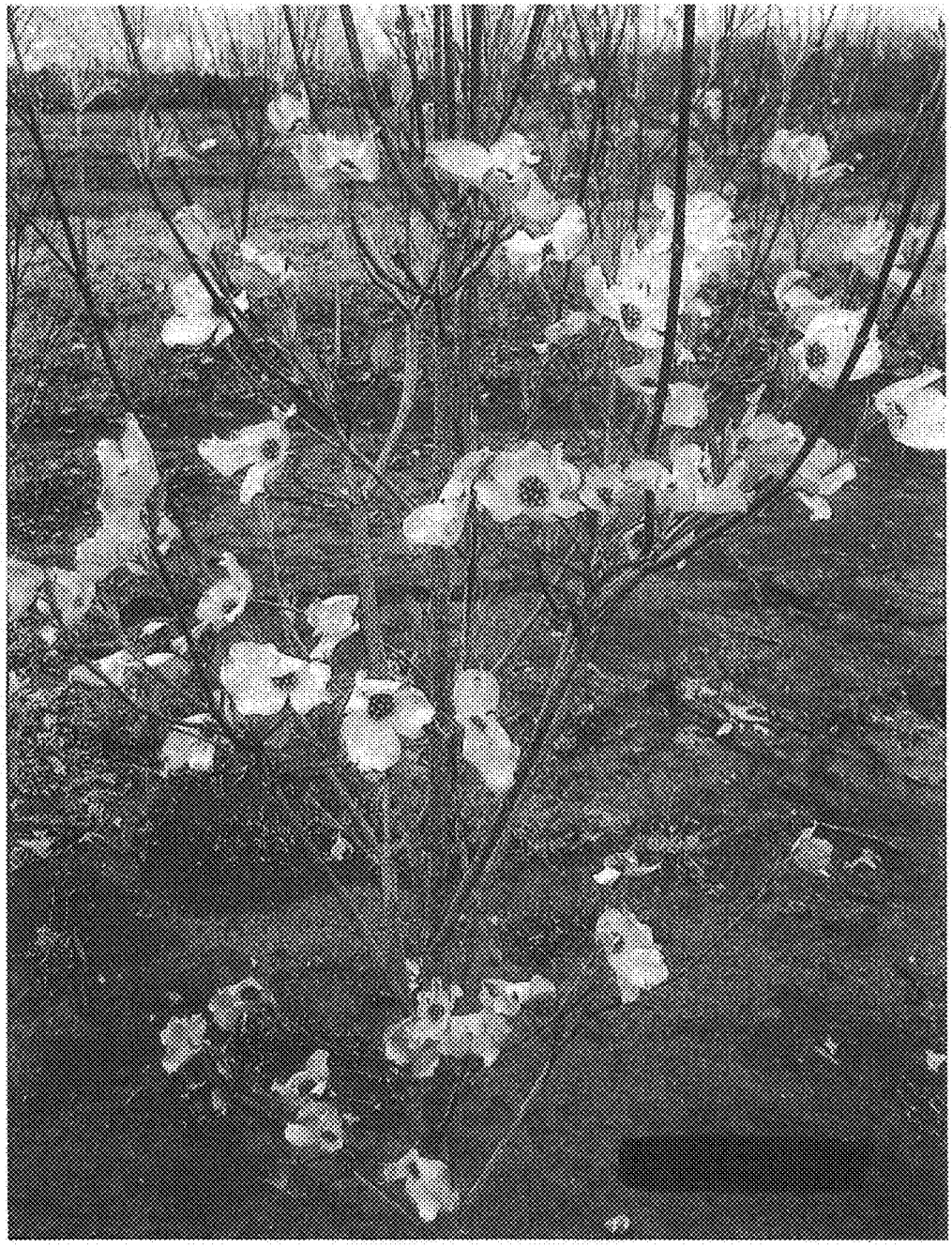
FIG. 1 depicts the bracts as they begin to open.
Figure 2:
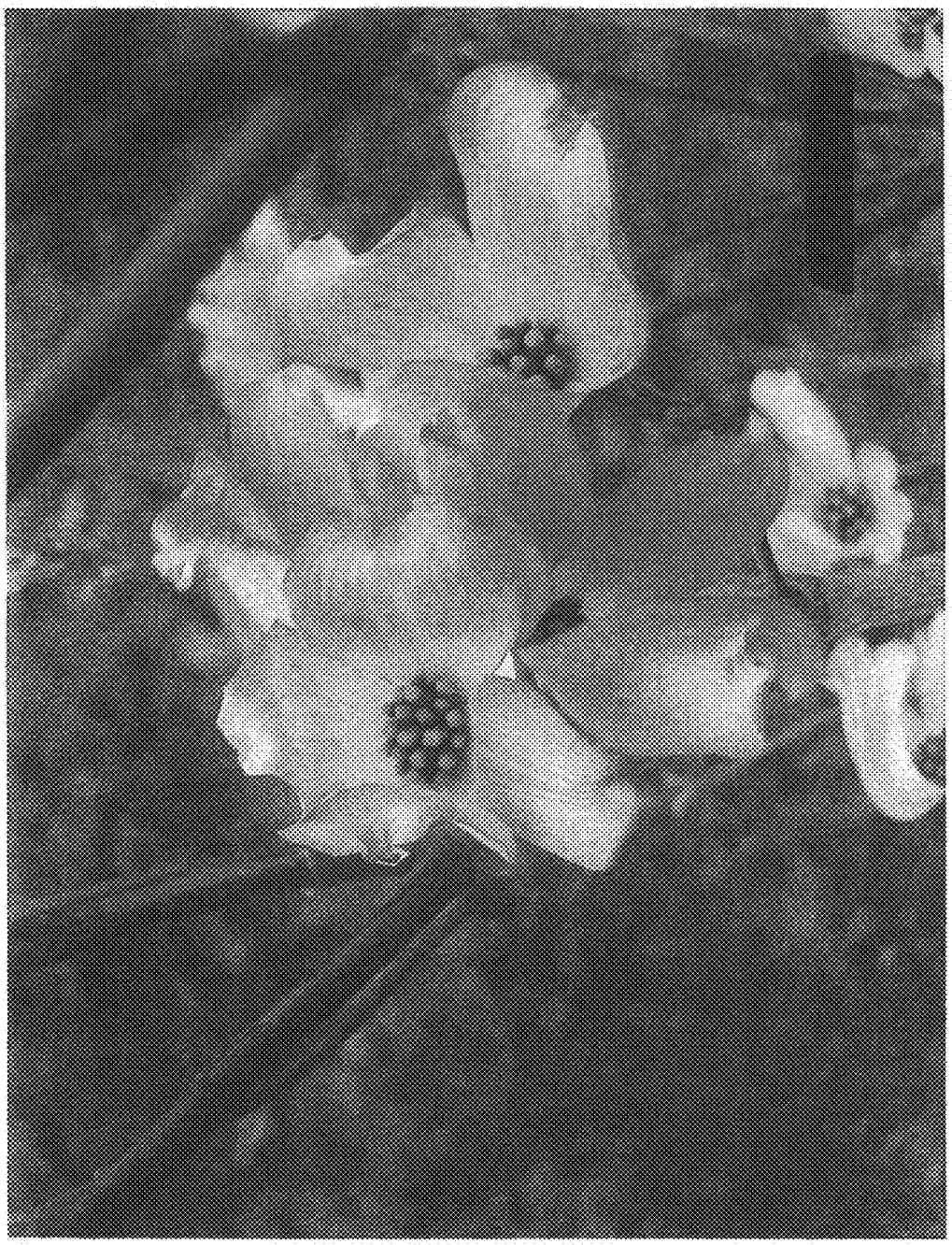
FIG. 2 depicts bract color early in the bloom period.
Figure 3:
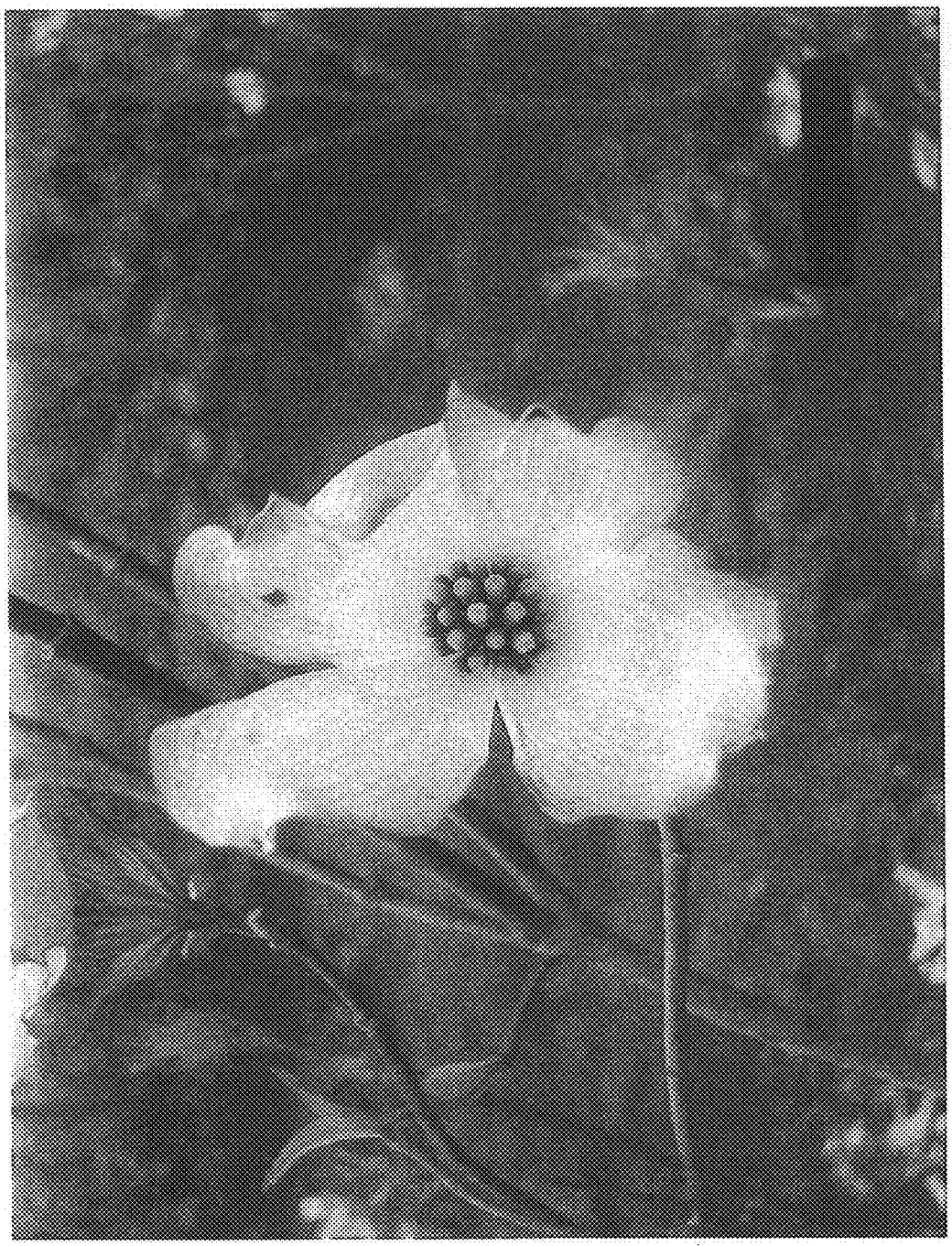
FIG. 3 depicts bract color in the early to middle bloom period.
Figure 4:
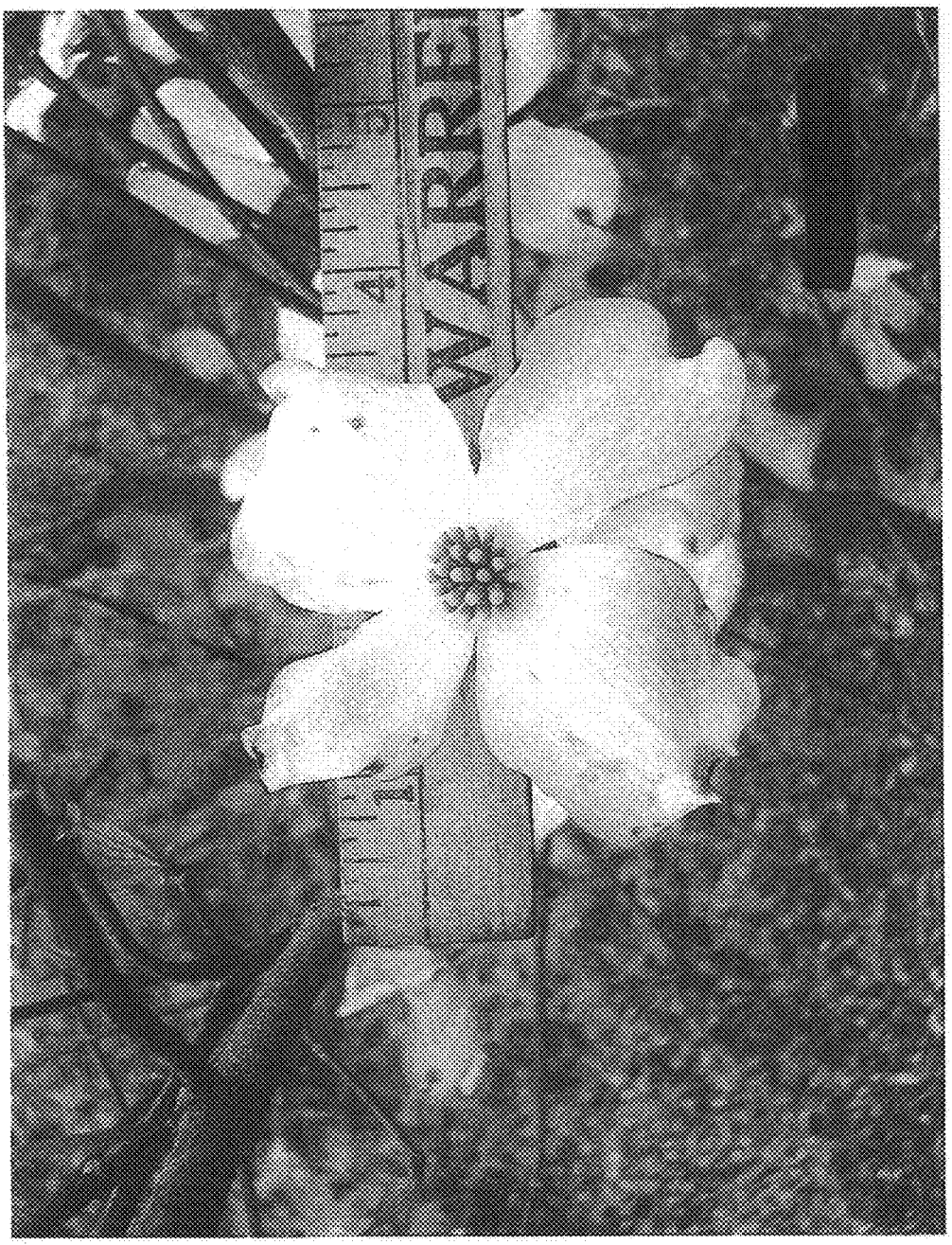
FIG. 4 depicts bract color in the middle of late bloom period.
Figure 5:
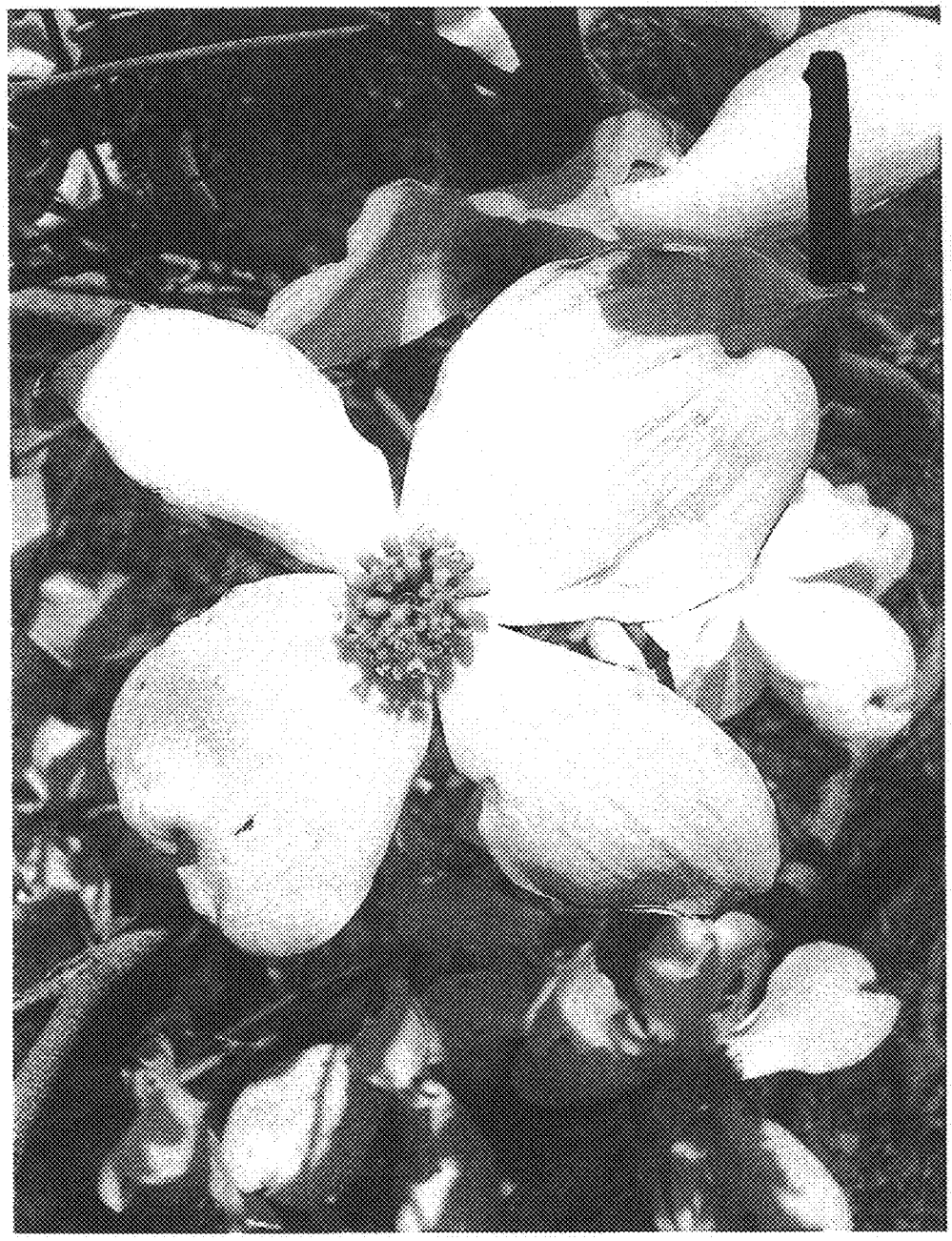
FIG. 5 depicts bract color late in the bloom period.

Flowers: [t] Typical of the species in size and shape. The true flowers are very small, greenish yellow (RHS 153D), and not showy. The showy parts are the bracts which are obovate or emarginate, are about 2 inches long, occur between April and May, and last for up to two weeks. There are four (4) bracts surrounding the true flower with each bract being 2.25 inches long and 1.5 inches wide at its widest point. The effect is that of a flower whose diameter is approximately 4.5 inches. These dimensions are averages and will vary from flower to flower and tree to tree depending upon cultural conditions. The bracts of my new tree 'NM1' are unique in the development of their coloration. As they open, the new bracts are purplish pink (RSH 73B) at the margins, becoming lighter pink (RHS 55B) in the middle of the bract. The center of the bracts is cream-colored (RHS 160A) as shown in FIG. 1. As flowering progresses, the center of the bracts, and sometimes the apical margins, fade; while, the lighter pink portions (RHS 73A) of the bract darken to a purplish red (RHS 67A) at the margins and tips. This is as shown in FIG. 2. The bracts are wide but do not overlap, and they twist slightly as they open. As the flowers develop between days 4-7 of the bloom period, the bracts fade to a light pink (RHS 68B), with darker pink veins and margins (RHS 68A). This is as shown in FIG. 3. During the next 3 to 4 days of flowering, the center and tips become lighter. The lighter pink (RHS 64D) fades to the darker pink (RHS 69C) still showing at the apical margins, and the bracts become substantially flat with only a slight undulation apparent as shown in FIG. 5. During all the stages, some pink spotting is evident. The true flowers are not showy and are borne in the center of the bracts in a flowering cyme measuring 0.75 inches across. They are green-yellow (RHS 1A) in color when fully open, perfect, and self-sterile.

Fruit: [Slightly] My new tree 'NM1' has borne fruit which is slightly larger than the species: a glossy red drupe (RHS 44A), ⅓ to ½ inches long and ⅓ to ⅜ inches wide, ovoid, in clusters of 3 to 4, ripening from September to October, and persisting into December. Each fruit contains a single seed.

Stem: Typical of the species: [reddish purple] green (RHS 144C), turning grayish (RHS 194A). Older wood becomes gray-brown (RHS 200C) and develops a blocky appearance.

Trunk: Typically a low-branched tree with multiple trunks and spreading branches. The tree can be trained to maintain a central leader in the nursery, but this will eventually be lost in the landscape. The bark of the trunk [becomes gray-brown to black] is gray (RHS 202C) and, with time, forms small, generally square shaped blocks which may become darker with age, as is typical of the species. My new tree is not old enough to display this characteristic.

Branching: Typical of these species: spreading horizontally, creating a layered effect. The branching of my new tree 'NM1' is upright in the nursery, which is typical of young dogwood trees. It is believed that the branching habit will remain typical of the species as the tree matures.

Root System: My tree 'NM1' is budded onto seedling rootstocks, so the root system is not known. I expect it is typical of the species, which is shallow and fibrous.

Growth habit: Growth is strong, producing a well-branched, upright, rounded canopy as a young tree. This is as shown in FIGS. 5 and 6.

Vigor: More vigorous than the species, producing up to 4 feet of growth as a young tree in a production setting, and outgrowing *Cornus Florida* 'Cherokee Princess', which is considered one of the faster growing cultivars.

Diseases: Seedling *Cornus Florida* can be affected by many diseases and insects. Leaves, stems, and bracts can be infected by anthracnose, leaf blight can be problematic in wet years, and various cankers will also infect the trees. Powdery mildew is the primary problem for trees in the nursery, and many resistant selections have been made. Many of these diseases are stress-related. However, my new tree 'NM1' has proven to be resistant to powdery mildew even when disease pressure is high, and I have observed no other disease problems.

Pests: Dogwood borer is a significant problem in the landscape, but less so in the nursery. At this time, I have observed no insect problems with my new tree.

The invention claimed is:

1. A new and distinct variety of Flowering Dogwood tree named 'NM1' substantially as herein shown and described, characterized particularly as to novelty by its pink bracts that fade to white over the bloom period, vigorous upright growth with good branching, and mildew resistance.

* * * * *